United States Patent [19]

Axen

[11] 4,073,803

[45] Feb. 14, 1978

[54] TRIPHENYLPHOSPHONIUM BROMIDE INTERMEDIATE FOR 2,2-FLUORO-PG ANALOGS

[75] Inventor: Udo F. Axen, Plainwell, Mich.

[73] Assignee: The Upjohn Company, Kalamazoo, Mich.

[21] Appl. No.: 724,154

[22] Filed: Sept. 17, 1976

Related U.S. Application Data

[62] Division of Ser. No. 552,708, Feb. 24, 1975, Pat. No. 4,001,300.

[51] Int. Cl.$^2$ ............................................. C07F 9/54
[52] U.S. Cl. ............................................. 260/515 A
[58] Field of Search ..................... 260/515 M, 515 A

[56] References Cited

U.S. PATENT DOCUMENTS

| | | | |
|---|---|---|---|
| 3,531,514 | 9/1970 | Redmore | 260/515 M |
| 3,736,349 | 5/1973 | Gillham et al. | 260/515 A |

*Primary Examiner*—Jane S. Myers
*Attorney, Agent, or Firm*—Robert A. Armitage

[57] ABSTRACT

2,2-Difluoro prostaglandin E, $F_\alpha$, $F_\beta$, A, and B analog are disclosed with intermediates and with processes for making them. These compounds differ from the prostaglandins in that they have two fluoro atoms at the C-2 position in place of the two hydrogen atoms at C-2 in the prostaglandins. These compounds are useful for a variety of pharmacological purposes, including anti-ulcer, inhibition of platelet aggregation, increase in nasal patency, labor induction at term, and wound healing.

1 Claim, No Drawings

TRIPHENYLPHOSPHONIUM BROMIDE INTERMEDIATE FOR 2,2-FLUORO-PG ANALOGS

The present application is a divisional application of Ser. No. 552,708, filed Feb. 24, 1975, now issued as U.S. Pat. No. 4,001,300, on Jan. 4, 1977.

The present invention relates to prostaglandin analogs for which the essential material constituting a disclosure therefor is incorporated by reference here from U.S. Pat. No. 4,001,300, issued Jan. 4, 1977.

I claim:

1. A phosphonium salt of the formula

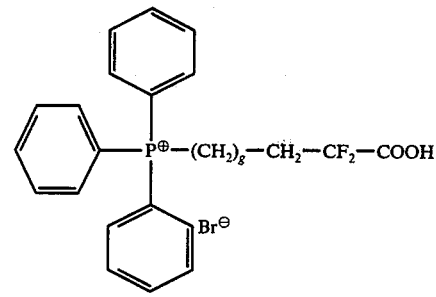

wherein $g$ is 2 to 4, inclusive.

* * * * *